United States Patent
Zhong et al.

(10) Patent No.: US 7,037,552 B2
(45) Date of Patent: *May 2, 2006

(54) COATING DISPENSING SYSTEM AND METHOD USING A SOLENOID HEAD FOR COATING MEDICAL DEVICES

(75) Inventors: Sheng-ping Zhong, Northborough, MA (US); Dennis R. Boulais, Danielson, CT (US); Praveen Kulkarni, Worcester, MA (US); Ron Sahatijian, Lexington, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/737,256

(22) Filed: Dec. 15, 2003

(65) Prior Publication Data

US 2004/0131755 A1    Jul. 8, 2004

Related U.S. Application Data

(63) Continuation of application No. 10/045,492, filed on Jan. 14, 2002, now Pat. No. 6,682,771, which is a continuation-in-part of application No. 09/895,415, filed on Jul. 2, 2001, now Pat. No. 6,676,987.

(51) Int. Cl.
*A61L 33/00* (2006.01)
*B05D 1/36* (2006.01)

(52) U.S. Cl. .................. 427/2.24; 427/261; 427/409
(58) Field of Classification Search ............ 427/2.24, 427/2.1, 2.25, 2.28, 2.3, 261, 286, 287, 256, 427/258, 259, 282, 409

See application file for complete search history.

(56) References Cited

U.S. PATENT DOCUMENTS 4,207,356 A    6/1980    Waugh (Continued)

FOREIGN PATENT DOCUMENTS

EP    0 850 651    7/1998

(Continued)

OTHER PUBLICATIONS

P. F. Blazdell, et al., "Application of a continuous ink jet printer to solid freeforming of ceramics" Journal of Materials Processing Technology 99, (2000) pp. 94-102.

(Continued)

*Primary Examiner*—Timothy Meeks
*Assistant Examiner*—Eric B. Fuller
(74) *Attorney, Agent, or Firm*—Kenyon & Kenyon LLP (57) ABSTRACT

System and method for coating a medical appliance are provided. In accord with one embodiment, a system for applying a coating to a medical appliance having accessible patterned surfaces is provided. The system may include: a processor, an appliance support, and a solenoid type fluid dispensing head having an electromagnetically controlled valve. In the system, the appliance support may be adapted to hold the medical appliance and to provide direct access for a coating to contact the exposed external patterned surfaces of the medical appliance. The solenoid type fluid dispensing head in this system may move with respect to the medical appliance and may be in communication with a source of coating and with the processor. The processor in this system may contain commands that instruct the solenoid type fluid dispensing head to force coating onto the accessible patterned surfaces of the medical appliance in a pattern that correlates with the accessible patterned surfaces of the medical appliance.

19 Claims, 8 Drawing Sheets

U.S. PATENT DOCUMENTS

| | | | |
|---|---|---|---|
| 4,743,252 | A | 5/1988 | Martin, Jr. et al. |
| 5,059,266 | A | 10/1991 | Yamane et al. |
| 5,104,400 | A | 4/1992 | Berguer et al. |
| 5,804,083 | A | 9/1998 | Ishii et al. |
| 5,935,331 | A | 8/1999 | Naka et al. |
| 6,056,993 | A | 5/2000 | Leidner et al. |
| 6,063,339 | A * | 5/2000 | Tisone et al. .................. 422/67 |
| 6,107,004 | A | 8/2000 | Donadio, III |
| 6,176,874 | B1 | 1/2001 | Vacanti et al. |
| 6,193,923 | B1 | 2/2001 | Leyden et al. |
| 6,287,628 | B1 * | 9/2001 | Hossainy et al. ............ 427/2.3 |
| 6,395,326 | B1 | 5/2002 | Castro et al. |
| 6,645,547 | B1 | 11/2003 | Shekalim et al. |
| 2004/0058084 | A1 | 3/2004 | Shekalim et al. |
| 2004/0076747 | A1 | 4/2004 | Shekalim et al. |
| 2005/0048194 | A1 | 3/2005 | Shmulewitz |

FOREIGN PATENT DOCUMENTS

WO    WO 01/91918    12/2001

OTHER PUBLICATIONS

Jin Hua Song, et al., "Formulation and Multilayer Jet Printing of Ceramic Inks", Journal of the American Ceramic Society Incorporating Advanced Ceramic Materials and Communications, vol. 82, No. 12, Dec. 1999, pp. 3374-3380.

Matthew Mott, et al., "Microengineering of Ceramics by Direct Ink-Jet Printing", Journal of the American Ceramic Society Incorporating Advanced Ceramic Materials and Communications, vol. 82, No. 7, Jul. 1999, pp. 1653-1658.

M. J. Wright, et al., "Ceramic Deposition using and Electromagnetic Jet Printer Station", Journal of Materials Science Letters 18, (1999), pp. 99-101.

D. A. Grigoriev, et al., "Preparation of Silicon Carbide by Electrospraying of a Polymeric Precursor", vol. 81, No. 4, (2001), pp. 285-291.

P. Miao, "Electrostatic Atomization of Ultra Fine Spray of Ceramic Solution", Institute of Physics Conference Series No. 163, Proceedings of the 10th International Conference, Cambridge Mar. 28-31, 1999, pp. 119-122.

Kitty A. M. Seerden, et al., "Ink Jet Printing of Wax-Based Alumina Suspensions", Journal of the American Ceramic Society Incorporating Advanced Ceramic Materials and Communications, vol. 84, No. 11, Nov. 2001, pp. 2514-2520.

J. R. G. Evans, et al., "Combinatorial Searches of Inorganic Materials using the Ink-Jet Printer: Science, Philosophy and Technology", Journal of the European Ceramic Society, vol. 21, No. 13, (2001), pp. 2291-2299.

P. F. Blazdell, et al., "Preparation of Ceramic Inks for Solid Freeforming Using a Continuous Jet Printer", Journal of Materials Synthesis and Processing, vol. 7, No. 6, Nov. 1999, pp. 349-356.

The Lee Company Electrofludic System, "Micro-Dispense Valves", 7th Edition 2000, 7 sheets.

* cited by examiner

COATING DISPENSING SYSTEM AND METHOD USING A SOLENOID HEAD FOR COATING MEDICAL DEVICES

RELATED APPLICATIONS

This application is a continuation of application Ser. No. 10/045,492, filed on Jan. 14, 2002 now U.S. Pat. No. 6,682,771, which is a continuation-in-part of application Ser. No. 09/895,415, filed on Jul. 2, 2001 now U.S. Pat. No. 6,676,987.

FIELD OF THE INVENTION

The present invention generally regards the coating of work-pieces. More particularly, the present invention regards a method and system for precision coating implantable medical appliances using a solenoid type fluid dispensing head.

BACKGROUND INFORMATION

The positioning and deployment of medical appliances within a target site of a patient is a common, often-repeated procedure of contemporary medicine. These appliances or implants are used for innumerable medical purposes including the reinforcement of recently re-enlarged lumens and the replacement of ruptured vessels.

Coatings are often applied to these medical appliances to increase their effectiveness. These coatings may provide a number of benefits including reducing the trauma suffered during the insertion procedure, facilitating the acceptance of the medical appliance into the target site, and improving the post-procedure effectiveness of the appliance.

Expandable stents, stent grafts, balloon delivery systems, and aneurism coils are specific examples of medical appliances or implants that may be coated and inserted within the body. Expandable stents are tube-like medical appliances that often have a mesh-like structure designed to support the inner walls of a lumen. These stents are typically positioned within a lumen and, then, expanded to provide internal support for it. Because of the direct contact of the stent with the inner walls of the lumen, stents have been coated with various compounds and therapeutics to enhance their effectiveness. When this coating is haphazardly applied or has somehow been removed during the stent's manufacture or delivery, the stent's effectiveness can be compromised. In certain circumstances, defective implanted stents must be removed and replaced through a second medical procedure—an unwanted result.

Indiscriminate coating methods such as dip-coating and spray-coating have been used to coat stents as well as other medical appliances. These methods are, however, both wasteful and difficult to control. For example, dipping can result in non-uniform application of the coating to the appliance, thereby placing more coating at one end or region of the stent and making it difficult to predict the dosage of therapeutic that will be delivered when the stent or other appliance is implanted. The indiscriminate nature of dipping is also problematic as it may lead to the cracking and crumbling of coating at the junctions, hinges, and flexing members of the mesh-like stents. The coating that covers the hinged portions of the stent is highly susceptible to exfoliation because, as the stent is expanded, intolerable stresses may develop within the coating.

Figure 1:
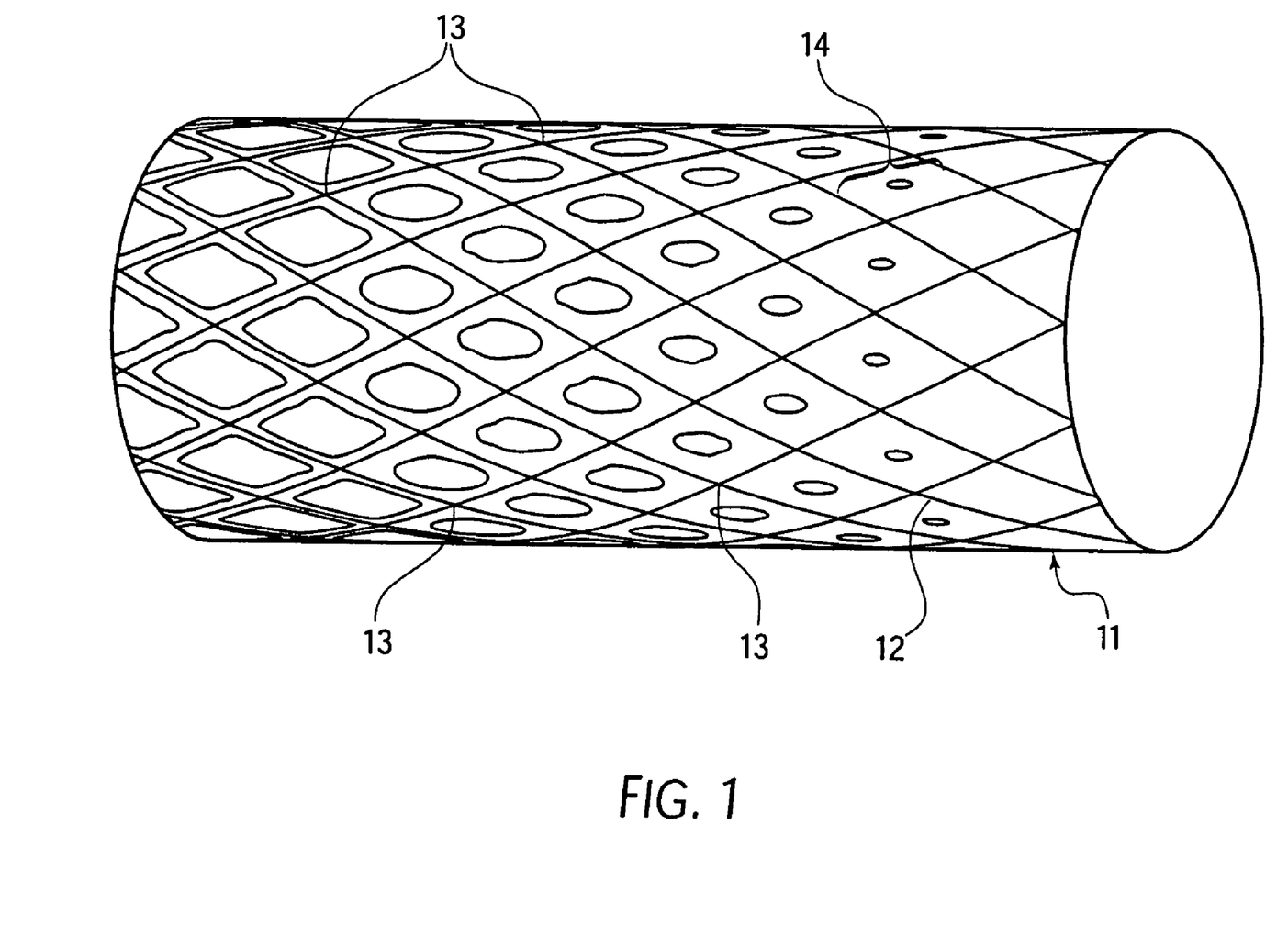
FIG. 1 is an enlarged view of a stent that has been unevenly coated with a coating.
Figure 2:
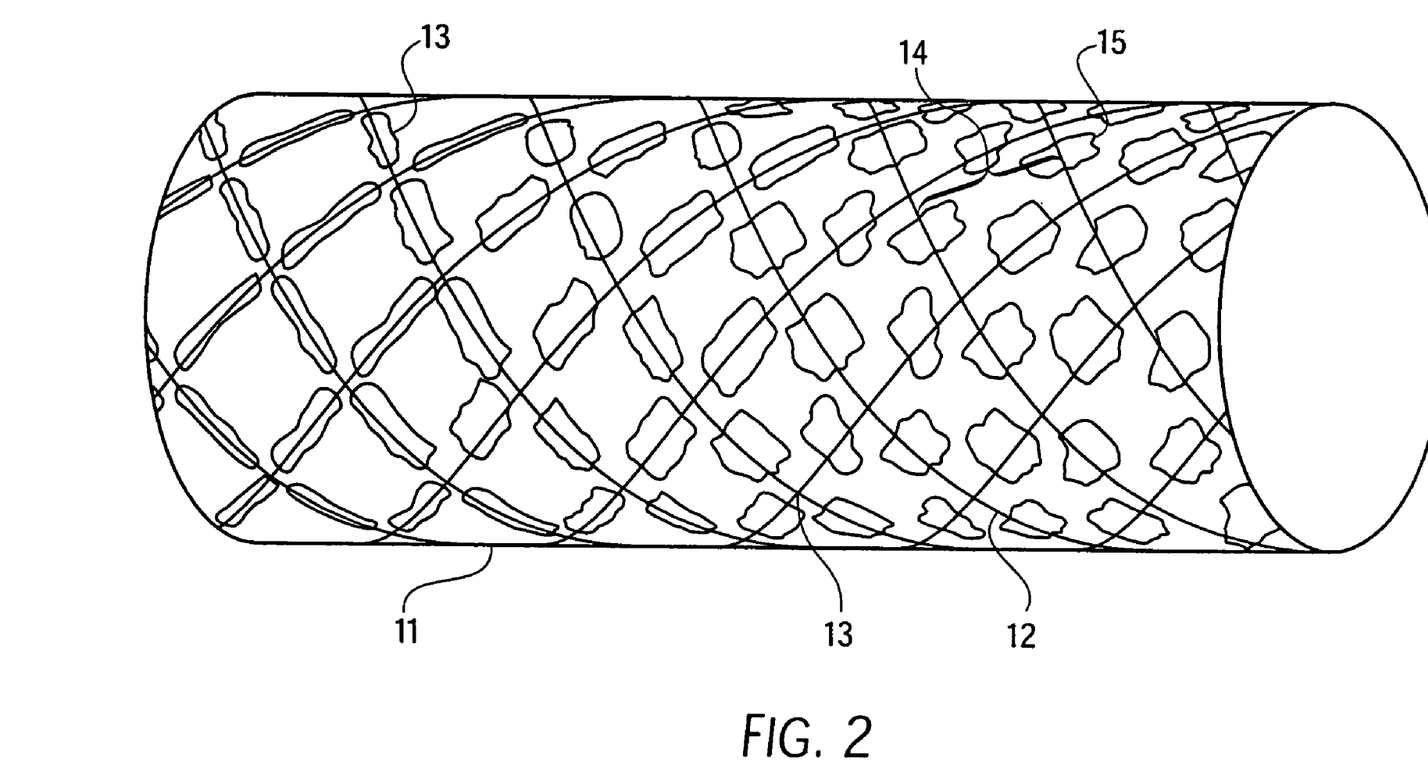
FIG. 2 is an enlarged view of the stent of FIG. 1 in an expanded state, the uneven coating being broken and cracked at the junction of the stent's struts.

FIGS. 1 and 2 are illustrative of some of the concerns stemming from an indiscriminate coating process like dipping. In FIG. 1, stent 11 is shown in a closed, pre-deployment state. Here, stent 11 has been previously dipped in a vat of therapeutic in the direction of arrow 16. In other words, the right side of stent 11 was the leading edge entering the dipping vat. As can be seen, the coating of stent 11 is heavier on the right side than on the left side and covers each of the junctions 13 throughout the entire stent 11. As can also be seen, the coating becomes progressively thicker and covers more of the space between each of struts 12 as you travel from the left side to the right side of stent 11. This increasing thickness of coating is indicative of a stent that has been dipped and let stand on one of its ends as the coating dries and adheres to the stent.

FIG. 2 shows the unevenly coated stent 11 of FIG. 1 in an expanded state as it may be after it is positioned within a body. As is evident, the expansion of stent 11 has led to the cracking and crumbling of coating 15. Also evident is that the coating has been removed from most if not all of the junction points 13 after stent 11 has been expanded.

SUMMARY OF THE INVENTION

A system and method for coating a medical appliance is provided. In accord with one embodiment, a system for applying a coating to a medical appliance having accessible patterned surfaces is provided. This system may include: a processor, an appliance support, and a solenoid type fluid dispensing head having an electromagnetically controlled valve. In this system the appliance support may be adapted to hold the medical appliance and to provide direct access for a coating to contact the exposed external patterned surfaces of the medical appliance. The solenoid type fluid dispensing head in this system may move with respect to the medical appliance and may be in communication with a source of coating and with the processor. The processor in this system may contain commands that instruct the solenoid type fluid dispensing head to force coating onto the accessible patterned surfaces of the medical appliance in a pattern that correlates with the accessible patterned surfaces of the medical appliance.

A method for applying a coating to a medical appliance having an accessible patterned surface is also provided. In one embodiment this method may include holding the medical appliance, providing direct access to the external surfaces of the medical appliance, and receiving command signals that instruct a solenoid type fluid dispensing head to force coating onto the accessible patterned surfaces of the medical appliance in a pattern that correlates with the accessible patterned surfaces of the medical appliance.

DETAILED DESCRIPTION

Figure 3:
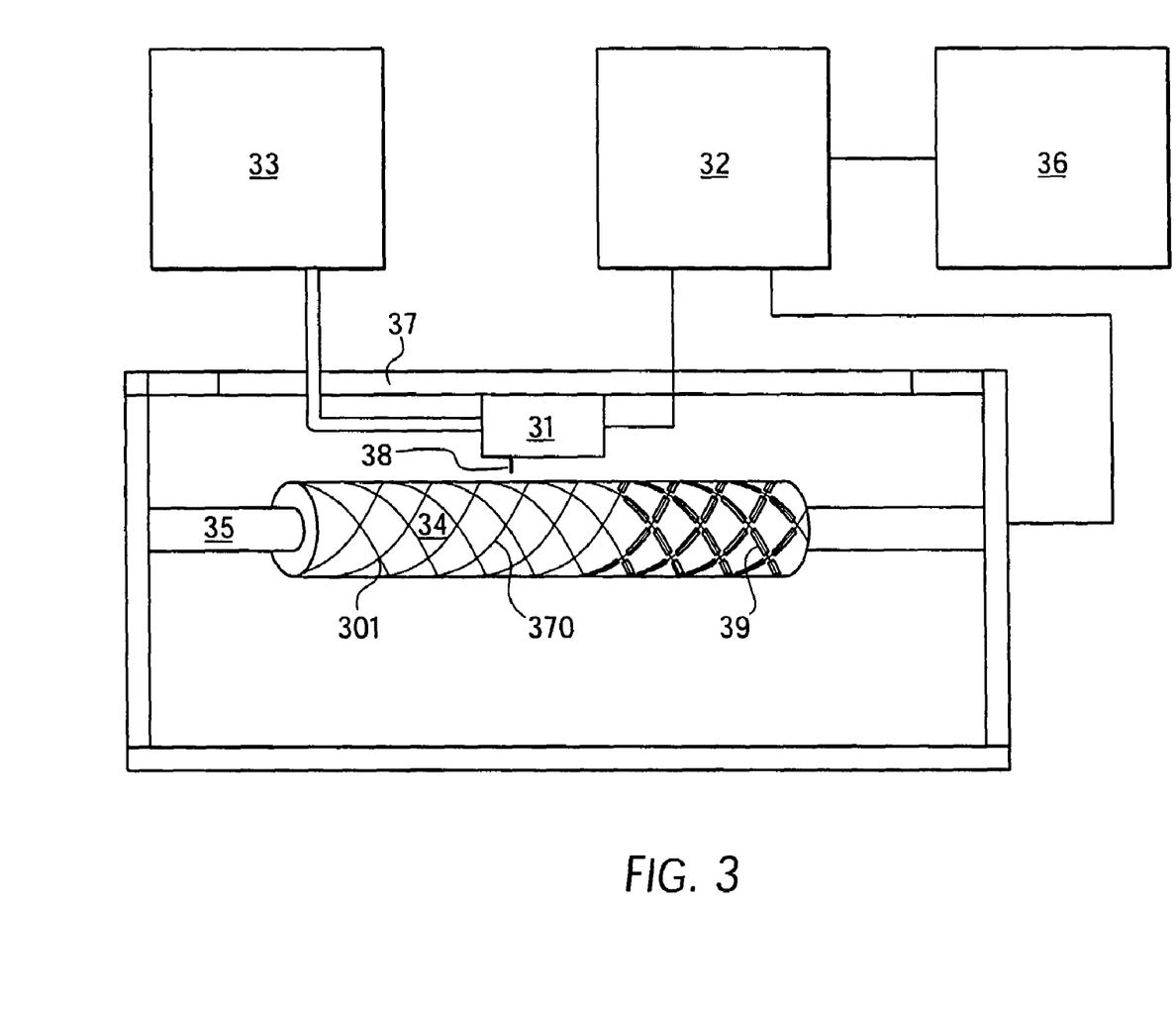
FIG. 3 is a schematic view of a system for applying a coating to a medical appliance using a solenoid type fluid dispensing head in accord with one embodiment of the present invention.

FIG. 3 illustrates a system for coating a medical appliance using a solenoid type fluid dispensing head in accord with one embodiment of the present invention. In this system, solenoid type fluid dispensing head 31 may be used to force coating onto the patterned surfaces of medical appliance 34. In this embodiment, solenoid type fluid dispensing head 31 may be placed in close proximity to medical appliance 34 and may be moved back and forth along track 37 so that it may be able to coat the entire external patterned surface of medical appliance 34. Solenoid type fluid dispensing head 31 may be controlled by, or at least receive signals from, processor 32, which may instruct it to coat only struts 370 of medical appliance 34. In other words, as solenoid type fluid dispensing head 31 slides back and forth along track 37 and as medical appliance 34 is spun on appliance support 35, solenoid type fluid dispensing head 31 may force coating onto struts 370 while concurrently refraining from forcing coating into spaces between struts 370, because coating forced into these spaces would simply be wasted or result in errant deposits of coating elsewhere on medical appliance 34.

As can be seen in FIG. 3, a portion 39 of struts 370 has already been coated, while another portion of struts 370 has not been coated. Also apparent in FIG. 3 is that junctions 301 of struts 370 have not been coated. FIG. 3 also illustrates stream of coating 38 ejected from solenoid type fluid dispensing head 31 prior to contact with medical appliance 34.

In FIG. 3, the coating source 33 may be in fluid communication with solenoid type fluid dispensing head 31 and may be used to supply coating to solenoid type fluid dispensing head 31. Storage media 36 may be in communication with processor 32 and may be used to store and provide instructions for processor 32 and coating source 33 for coating medical appliance 34. Storage media 36 may be one of numerous types of available storage media including both volatile (i.e. RAM) and non-volatile storage devices (i.e. ROM, CD ROM, EEPROM, Magnetic Media, etc.). The pre-programmed instructions or other retained data may be unique to each medical appliance 34 and may account for the unique external pattern and precise dimensions of each medical appliance 34 that may be coated by solenoid type fluid dispensing head 31. Storage media 36 may also hold unique instruction sets for many different medical appliances or may be provided with a media receptacle such as a disk drive that accommodates different recordable media, each recordable media holding a unique instruction set for a single medical appliance or a set of instructions for multiple medical appliances.

As mentioned above, medical appliance 34 in this embodiment may be rotated by appliance support 35 in order to expose different sides of medical appliance 34 to solenoid type fluid dispensing head 31. Consequently, through the coordinated movement of solenoid type fluid dispensing head 31 on track 37 and medical appliance 34 in appliance support 35, all external portions of medical appliance 34 may be exposed to and coated by the nozzle (not shown) of solenoid type fluid dispensing head 31.

In an alternative embodiment, wherein the medical appliance is flat or otherwise linear, the appliance support configuration may be different than that described above. Here, the appliance support may provide for movement of the appliance in both the x and y planes while the solenoid type fluid dispensing head moves back and forth overhead in order to reach the entire surface of the medical device.

As described above, solenoid type fluid dispensing head 31 may be in fluid communication with coating source 33. Coating source 33 may contain any one of several possible coatings to be placed on medical appliance 34. These coatings may include paclitaxel, a polymer with a suspended therapeutic, a non-thrombogenic agent, a lubricious material, a non-slippery material, a radiopaque agent, a radioactive agent, and a magnetic signature agent. These coatings may also include: pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflanimatory agents such as dexamethasone, prednisolone, corticosterone, budesonide, estrogen, sulfasalazine, acetyl salicylic acid, and mesalaniine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anticoagulants such as D-Phe-Pro-Arg chioromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof Cells may be of human origin (autologous or allogenic) or from an animal source (xenogeneic), genetically engineered if desired. The delivery medium is formulated as needed to maintain cell function and viability. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention may also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that may be injected, or whose DNA may be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which may be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins may be provided as homodimers, heterodimers, or combinations thereof, alone or together with other molecules. Alternatively or, in addition, molecules capable of inducing an upstream or downstream effect of a BMP may be provided. Such molecules include any of the "hedgehog" proteins, or the DNA's encoding them.

Another alternative coating material is any conductive material, which may be coated on the medical appliance to provide electrical conductivity for either power or signal functions to different parts of the medical appliance. For instance, an electrically conductive stripe may be applied to a catheter to enable a source of power at a proximal end of the catheter to provide power to a remote application at a distal end of the catheter. Additionally, the solenoid type fluid dispensing head may be utilized to coat a previously applied conductive material with an insulating material to thereby electrically isolate the conductive material.

A solenoid type fluid dispensing head may enable coating with more viscous materials than alternative methods because it may have a larger orifice and nozzle through which the coating fluids travel. Solenoid type fluid dispensing heads may enable coating with materials having viscosities from 1 centipoise (viscosity equal to water) to 1500 centipoise. Higher viscosities may also be possible using higher pressures for the coating source. An exemplary pressure for the coating source is 30 pounds per square inch above atmospheric pressure. Highly viscous materials may be preferable for coating medical appliances. Coating materials may become viscous due to a high solids content, which may be due to a higher concentration of therapeutic. A higher concentration of therapeutic may be preferable from a clinical standpoint in that it may make the medical appliance more effective. Additionally, coatings having high concentrations of therapeutic (and therefore high viscosity) may require fewer coating steps, and therefore require less time to produce. Therefore, higher drug loads may be applied to the medical appliance with fewer coats which may be applied in less time.

The solenoid type fluid dispensing head in this embodiment is preferably programmed to coat in a precise manner, allowing coating to be applied in a complex pattern, matching the complex pattern of the medical appliance. It may also be preferred that the stream of coating forced from the solenoid type fluid dispensing head be small in relation to the target area of the medical appliance to allow for a high degree of precision in coating the target. Precision coating of the medical appliance enables economical use of coating materials.

In an alternative embodiment, rather than having the coating material deposited in one coat or layer around the entire device, the solenoid type fluid dispensing head may coat the medical appliance with different layers of different thicknesses in different regions of the appliance as may be desirable for the subsequent use of the appliance. In doing so, different concentrations of therapeutic may be deposited in different regions of the medical appliance.

The coatings that may be applied by a solenoid type fluid dispensing head may also include: lubricious coatings to reduce the stress exerted on the stent during the stent's deployment; radiopaque coatings for identifying the location of stents after implantation using traditional radiography techniques; radioactive agents that are useful in preventing tissue regrowth in and around implanted stents; and magnetic coatings that enable identification of the location of the implanted stent using Magnetic Resonance Imaging (MRI) techniques. These magnetic coatings may be obtained using ferritic powders or paramagnetic powders such as Gadolinium or Disprosium.

Another useful application of this precise coating method may be to convey information, or an identification code on the appliance itself. This information or code may then be used to identify the source of the medical appliance and other history related to it for tracking purposes. Once implanted, the code, which may be a bar code, could be read though radiography, MRI or any other suitable invasive or non-invasive procedure.

Figure 4:
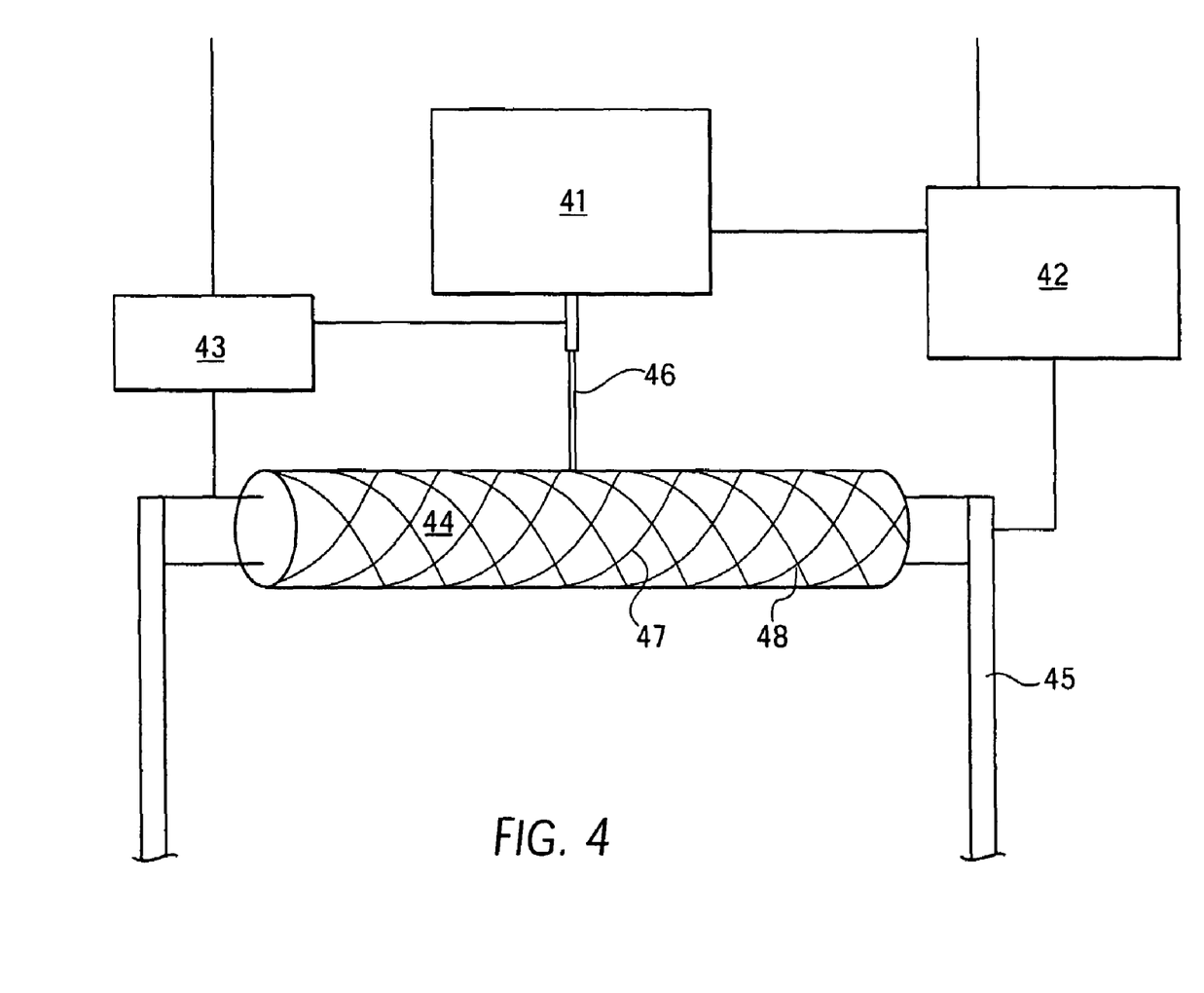
FIG. 4 is a schematic view of a system for applying a coating to a medical appliance using a solenoid type fluid dispensing head in accord with another embodiment of the present invention.

FIG. 4 shows a system for coating a medical appliance using a solenoid type fluid dispensing head and means for redirecting the material forced from the solenoid type fluid dispensing head prior to impacting the targeted medical appliance in accord with an alternative embodiment of the present invention. In this embodiment the solenoid type fluid dispensing head 41 may be used to coat a medical appliance 44 as described above. However, in this embodiment, after coating stream 46 has been forced from solenoid type fluid dispensing head 41, it may be redirected or influenced by redirecting means 43. Redirecting means 43 may be implemented using a battery or power source controlled by processor 42 to apply a voltage between nozzle 49 and appliance support 45. Alternative methods for influencing the path or trajectory of the coating once it has been forced from solenoid type fluid dispensing head 41 may also be possible. By employing redirecting means 43, the distance that the head may travel may be reduced. Similarly, the head may not need to be moved back and forth as quickly as in earlier embodiments as the gross adjustments may be completed with the movement of solenoid type fluid dispensing head 41 along a track (not shown) while the fine adjustments of the forced coating may be controlled by redirecting means 43.

In this embodiment, solenoid type fluid dispensing head 41 may be controlled by processor 42, which may also control appliance support 45 and redirecting means 43. Here, solenoid type fluid dispensing head 41, working in concert with appliance support 45, which may hold, move, and rotate the medical appliance 44, may coat each of the struts 47 but not the junctions 48 as shown in FIG. 4. Redirecting means 43 may be mounted so that coating stream 46 forced from solenoid type fluid dispensing head 41 receives a positive or negative charge from nozzle 49 which is connected to redirecting means 43. An opposite charge is applied by redirecting means 43 to the struts of medical appliance 44 through appliance support 45. Coating stream 46, having an opposite charge, would therefore be attracted to the struts of medical appliance 44.

Figure 5:
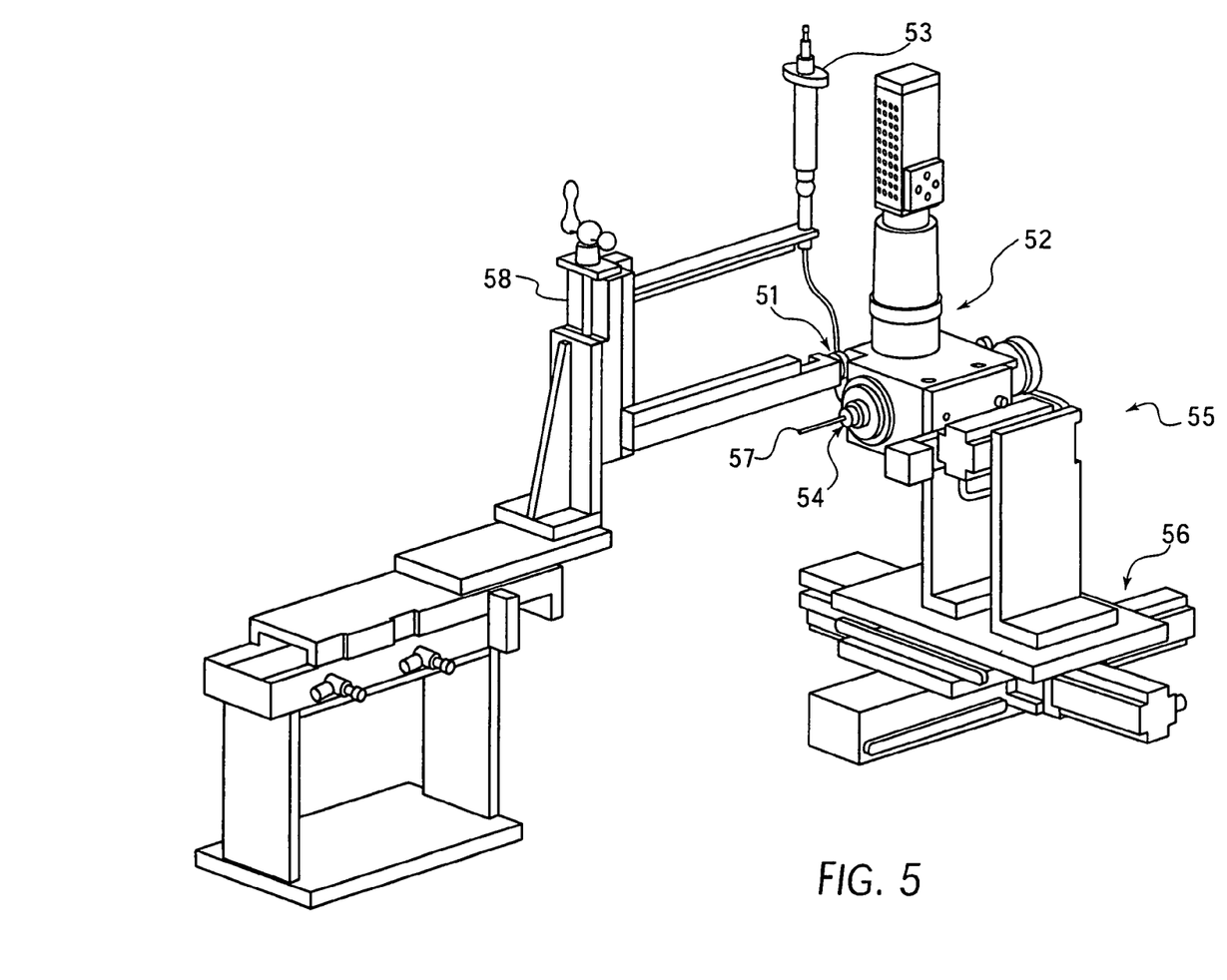
FIG. 5 is a schematic view of a solenoid type fluid dispensing head, appliance support, and microvision system in accord with another embodiment of the present invention.

FIG. 5 shows an alternative embodiment of the present invention wherein solenoid type fluid dispensing head 51 is in fluid communication with coating source 53. In FIG. 5, solenoid type fluid dispensing head 51 is arranged above medical appliance 54 which is arranged on appliance support 55. Solenoid type fluid dispensing head 51 is adjustable up and down by nozzle height adjustment 58 to increase or decrease the distance between solenoid type fluid dispensing head 51 and medical appliance 54. In one exemplary embodiment, the distance between solenoid type fluid dispensing head 51 and medical appliance 54 may depend on both the diameter of the nozzle (not shown) of solenoid type fluid dispensing head 51 and the viscosity of the fluid being applied to medical appliance 54. An exemplary range of values for the diameter of the nozzle is from 1 micron to 5 millimeters. Solenoid type fluid dispensing head 51 may also move in the direction of the longitudinal axis of medical appliance 54 during the coating process at the command of the processor.

Also shown in FIG. 5 is vision system 52 which is a microvision system or micro-tracking vision system. Vision system 52 communicates with a processor (not shown) to control the movements of solenoid type fluid dispensing head 51, the rotation of medical appliance 54, and the ejection of material from solenoid type fluid dispensing head 51. Vision system 52 may be used in any one of, or any combination of, the following ways. First, vision system 52 may be used to determine the position and orientation of medical appliance 54 by identifying an identifiable feature on medical appliance 54. Second, vision system 52 may be used to determine the position and orientation of the nozzle of solenoid type fluid dispensing head 51 by observing the solenoid type fluid dispensing head directly or by observing a test coating ejected onto a test piece for the purpose of locating solenoid type fluid dispensing head 51. Finally, vision system 52 may be used to monitor the coating of medical appliance 54 by solenoid type fluid dispensing head 51 as the coating is proceeding.

FIG. 5 illustrates appliance support 55, which includes both x-y positioning table 56 and mandrel 57. X-y positioning table 56 is used to position medical appliance 54 prior to, or during, the coating process. The x-y plane is defined as the plane perpendicular to the direction of the nozzle (not shown) of solenoid type fluid dispensing head 51. X-y positioning table may be either manually controlled or processor controlled. Mandrel 57 holds medical appliance 54, which in FIG. 5 is a stent, in a weak friction fit. Mandrel 57 in an exemplary embodiment is stainless steel with a teflon coating to prevent accumulation of any excess coating and to facilitate cleaning of mandrel 57. Additionally, mandrel 57 may be painted black to improve contrast between mandrel 57 and medical appliance 54 and to thereby improve the quality of the image collected by vision system 52.

Figure 6:
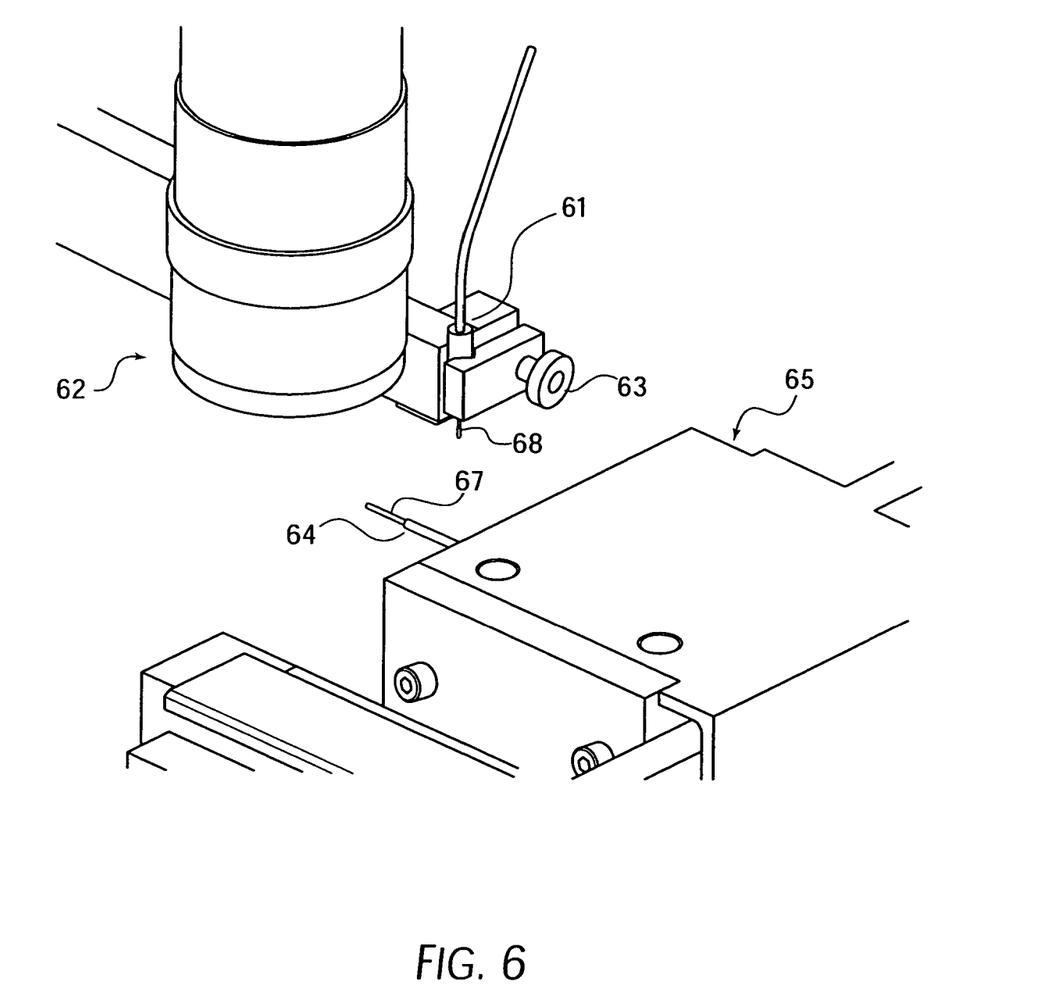
FIG. 6 is an enlarged view of the system shown in FIG. 5 showing the solenoid type fluid dispensing head and the microvision system.

FIG. 6 is an enlargement of the exemplary embodiment shown in FIG. 5. Solenoid type fluid dispensing head 61 is shown in valve mounting clamp 63. Also shown in FIG. 6 is vision system 62, which operates, as noted above, to observe the deposition of the coating onto medical appliance 64 as well as to perform numerous other functions including verifying the position of solenoid type fluid dispensing head 61 and medical appliance 64. In this embodiment, vision system 62 may be used for quality control, for orienting medical appliance 64 with respect to solenoid type fluid dispensing head 61, and for tracking the external pattern of medical appliance 64 during the coating process. Therefore, the processor may use information received from vision system 62 to adjust the commands it issues to solenoid type fluid dispensing head 61 during the coating process. Also illustrated in greater detail in FIG. 6 is appliance support 65, which includes mandrel 67, holding in this exemplary embodiment a stent as medical appliance 64. The position of mandrel 67 is adjustable by appliance support 65 in response to the processor using data collected by vision system 62. Mandrel 67 is rotatable before and during the coating process to bring all exposed surfaces of medical appliance 64 adjacent to solenoid type fluid dispensing head 61. When an exposed surface of medical appliance 64 that requires coating is adjacent to the solenoid type fluid dispensing head 61, solenoid type fluid dispensing head 61 is activated by the processor to open and allow the coating material, which is under pressure, to flow through solenoid type fluid dispensing head 61 and through nozzle 68 onto medical appliance 64. Nozzle 68 is adapted to provide maximum control over the coating material to allow accurate coating of medical appliance 64. The design of nozzle 68 may vary depending on the viscosity of the coating material. Alternatively, two solenoid type fluid dispensing heads may be connected to one nozzle 68 to provide the ability to coat medical appliance 64 with two different coatings. The different coatings may consist of different concentrations of the same therapeutic, the same therapeutic dissolved in different polymers or in different suspension fluids having different release rates, different therapeutics, or a combination of therapeutic materials and non-therapeutic materials (for instance lubricious materials) of any type noted above.

Figure 7:
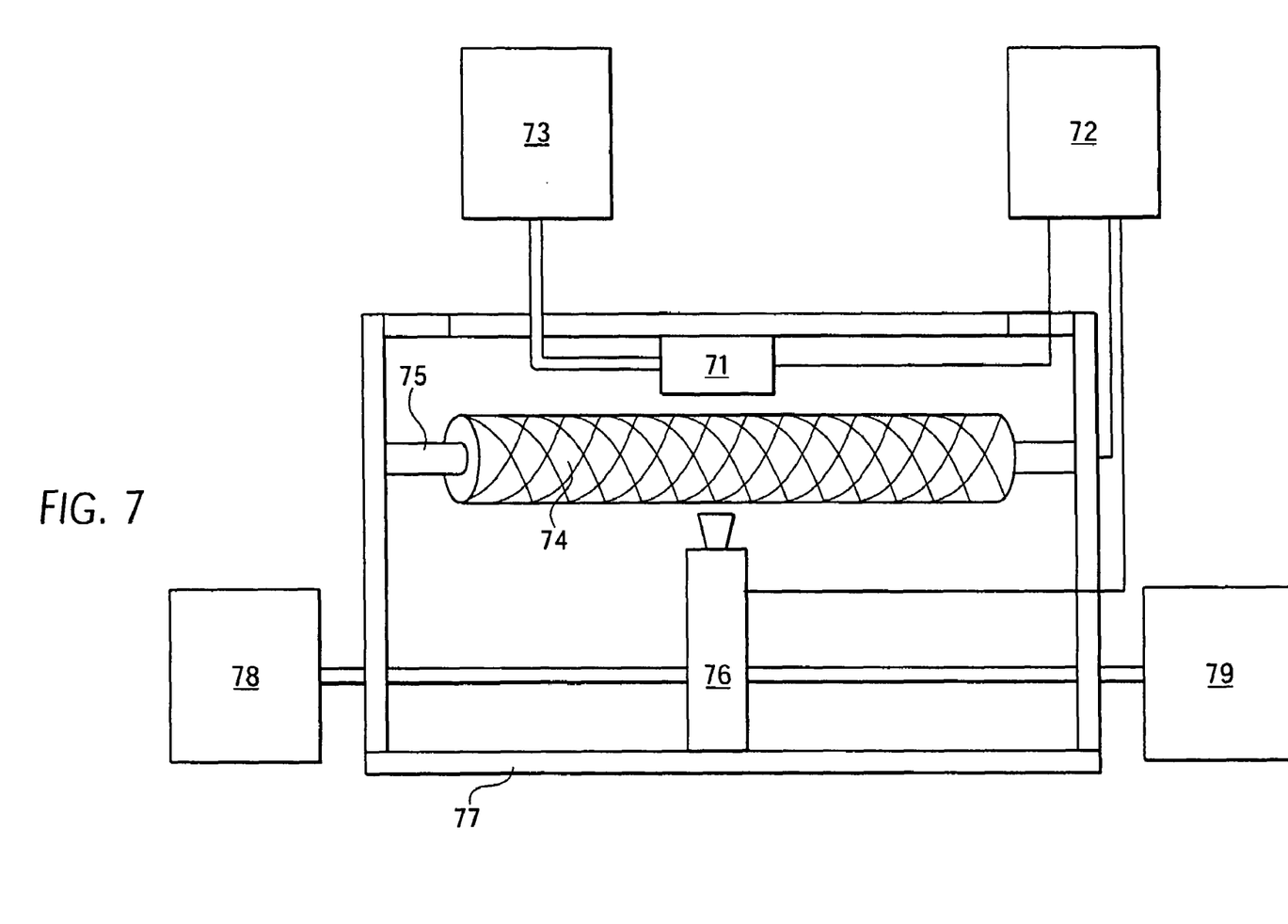
FIG. 7 is a schematic view of a system for applying a coating to a medical appliance using a solenoid type fluid dispensing head in accord with another embodiment of the present invention.

FIG. 7 shows a system for coating a medical appliance using a solenoid type fluid dispensing head in accord with another alternative embodiment of the present invention.

Solenoid type fluid dispensing head 71 is shown in FIG. 7 as mounted on support 77 and in fluid communication with coating source 73. Also evident in FIG. 7 are appliance support 75, sprayer 76, first sprayer source 78, and second sprayer source 79.

In this embodiment, rather than applying a coating material with solenoid type fluid dispensing head 71, a masking material may be applied. Once applied in a desirable pattern on medical appliance 74, an etchant may then be applied with sprayer 76 to etch the exposed portions of medical appliance 74 thereby etching the appliance in all regions not covered by the masking material. Then, once all the required etching is completed the masking material may be removed.

Sprayer 76 in this embodiment may be mounted on support 77 and may be able to slide back and forth along support 77 during the spraying activities. Sprayer 76 may also be in fluid communication with first sprayer source 78 and second sprayer source 79, similar to the coating sources described above, which may store different etching materials for use in the process.

Sprayer 76 in this embodiment may also be used for other indiscriminate spraying applications as well, including direct etching, cleaning, and drying medical appliance 74. In a direct etching application, solenoid type fluid dispensing head 71 may be used to apply a corrosive material onto medical appliance 74. Here the corrosive material may be used to selectively etch or groove portions of the various struts of medical appliance 74. Alternatively, solenoid type fluid dispensing head 71 may apply a first material to specific areas to be etched and, then, may apply a second material, which reacts with the first material, to etch the desired portions of medical appliance 74.

Figure 8:
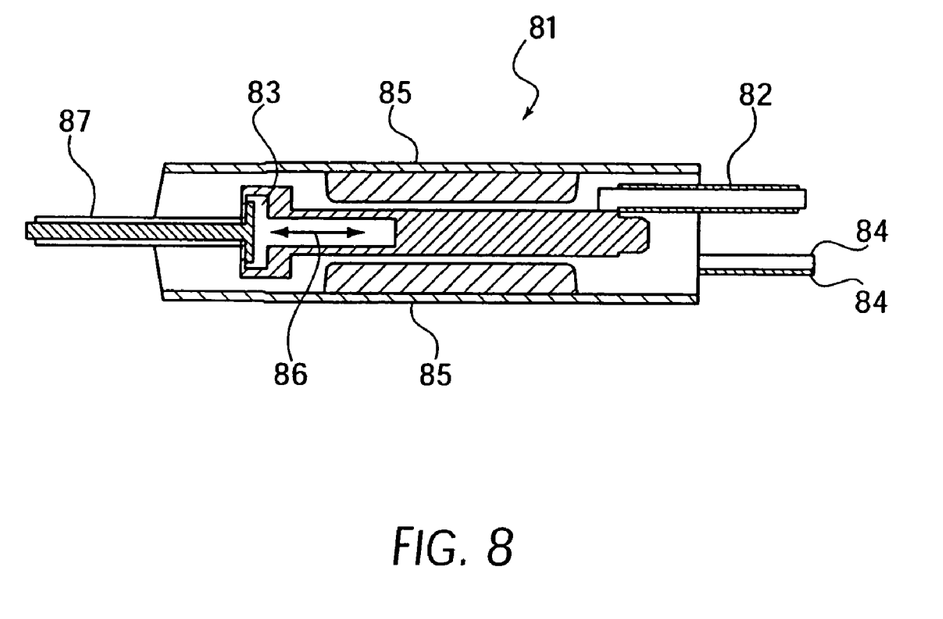
FIG. 8 is an enlarged cross-sectional view of a solenoid type fluid dispensing head in accord with another embodiment of the present invention.

FIG. 8 is an enlarged cross-sectional view of a solenoid type fluid dispensing head in accord with the present invention. Solenoid type fluid dispensing head 81 is a normally closed electromagnetically controlled valve having inlet 82 which connects to a pressurized coating source (not shown). The coating does not normally flow through solenoid type fluid dispensing head 81 because poppet 83 seals the passage to nozzle 87 under the influence of a spring (not shown). However, when a voltage is applied across contacts 84, current flows through coil 85, and an electromagnetic force is consequently applied to poppet 83. Poppet 83 is thereby induced to move in the direction of arrow 86, opening the passage and allowing the coating to flow. When poppet 83 is in the open position, the coating flows out through nozzle 87 onto the medical appliance (not shown). The wetted surfaces of solenoid type fluid dispensing head 81 are defined as those surfaces which contact the coating as it flows through solenoid type fluid dispensing head 81. In one alternative embodiment, the wetted surfaces are made of materials which are resistant to dissolving by Toluene and alcohol-based materials. The wetted surfaces may be constructed of EPDM, PEEK, stainless steel, glass, ceramic, PPS, epoxy, or any other appropriate material. Applying a voltage at contact 84 induces a continuous flow of coating out of nozzle 87, thereby enabling a thicker coating on the medical appliance with fewer passes required by solenoid type fluid dispensing head 81 over the specified portions of the medical appliance to achieve the desired coating thickness. Nozzle 87 is a non-contact nozzle designed to eject the coating material in a controlled fashion from a distance at the medical appliance. The distance between the nozzle and the medical appliance may depend on the viscosity of the fluid being ejected. The diameter of the nozzle may be in the range of 1 micron to 5 millimeters.

A solenoid type fluid dispensing head for coating a medical appliance is provided herein. While several embodiments have been discussed, others, within the invention's spirit and scope, are also plausible. For example, while one solenoid type fluid dispensing head is described in each of the above embodiments more than one solenoid type fluid dispensing head may also be employed. In this alternative embodiment, the multiple solenoid type fluid dispensing heads may work synchronously and asynchronously and may be ganged together to coat several medical appliances simultaneously.

What is claimed is:

1. A method for applying a coating to a stent comprising the steps of:
   providing a stent to be coated, the stent comprising a plurality of struts connected at a plurality of junctions;
   supporting the stent for coating;
   placing a first agent into a first chamber connected to a first solenoid fluid dispensing head;
   placing the first agent under pressure such that the first agent is dispensed from the first solenoid dispensing head when the first solenoid dispensing head is open and the first agent is not dispensed from the first solenoid dispensing head when the first solenoid dispensing head is closed;
   providing a processor to control the opening and closing of the first solenoid valve dispensing head;
   rotating the stent with respect to the first solenoid fluid dispensing head;
   opening the first solenoid fluid dispensing head when a strut of the stent that is desired to be coated with the first agent is adjacent the first solenoid fluid dispensing head, thereby causing the first agent to be dispensed from the first solenoid fluid dispensing head onto the desired strut of the stent; and
   closing the first solenoid fluid dispensing head when a junction of the stent is adjacent the first solenoid fluid dispensing head, thereby preventing the pressurized first agent from being dispensed from the first solenoid fluid dispensing head onto the junction.

2. The method of claim 1 wherein the first agent includes at least one of:
   a drug suspended in a polymer, a non-thrombogenic agent, a lubricious material, a non-slippery material, a radioactive agent, and a magnetic material.

3. The method of claim 1 wherein the first agent includes a therapeutic agent.

4. The method of claim 1 further comprising:
   forcing a second agent from a second solenoid fluid dispensing head onto the stent.

5. The method of claim 4 wherein at least one of the first agent and the second agent includes at least one of:
   a drug suspended in a polymer, a non-thrombogenic agent, a lubricious material, a non-slippery material, a radioactive agent, and a magnetic material.

6. The method of claim 4 wherein the first solenoid fluid dispensing head and the second solenoid fluid dispensing head are in fluid communication with a common nozzle.

7. The method of claim 4 wherein the second agent includes a therapeutic agent.

8. A method for applying a coating to a stent comprising the steps of:
   providing a stent to be coated;
   supporting the stent for coating;
   connecting a source of a coating material to a solenoid fluid dispensing head;

placing the coating material under continuous pressure such that the coating material is dispensed from the solenoid fluid dispensing head when the solenoid fluid dispensing head is activated;

providing a processor to control the opening and closing of the solenoid fluid dispensing head;

moving at least one of the stent or the solenoid fluid dispensing head to cause relative movement between the stent and the solenoid fluid dispensing head;

opening the solenoid fluid dispensing head when a part of the stent that is desired to be coated with the coating material is adjacent the solenoid fluid dispensing head, thereby causing the coating material to be dispensed from the solenoid fluid dispensing head onto the desired part of the stent; and closing the solenoid fluid dispensing head when no part of the stent that is desired to be coated with the coating material is adjacent the solenoid fluid dispensing head, thereby preventing the coating material from being dispensed from the solenoid fluid dispensing head, wherein the step of closing the solenoid fluid dispensing head comprises refraining from dispensing the coating material onto junctions between struts of the stent.

9. The method of claim 8 wherein the coating material comprises a therapeutic agent.

10. The method of claim 8 wherein the coating material comprises a therapeutic agent suspended in a polymer.

11. The method of claim 8 wherein the step of closing the solenoid fluid dispensing head further comprises refraining from dispensing the coating material into spaces between struts of the stent.

12. The method of claim 8 wherein the step of moving at least one of the stent or the solenoid fluid dispensing head includes rotating the stent.

13. The method of claim 8 wherein the step of moving at least one of the stent or the solenoid fluid dispensing head includes sliding the solenoid fluid dispensing head in a linear direction.

14. A method for applying a coating to a stent comprising the steps of:

providing a stent to be coated;

supporting the stent for coating;

connecting a source of a coating material to a dispensing head;

placing the coating material under continuous pressure such that the coating material is dispensed from the dispensing head when the dispensing head is activated;

providing a processor to control the dispensing of coating by the dispensing head;

moving at least one of the stent or the dispensing head to cause relative movement between the stent and the dispensing head;

controlling the dispensing of coating material such that the coating material is dispensed from the dispensing head when a part of the stent that is desired to be coated with the coating material is adjacent the dispensing head, thereby causing the coating material to be dispensed from the dispensing head onto the desired part of the stent; and controlling the dispensing of coating material such that the coating material is not dispensed from the dispensing head when no part of the stent that is desired to be coated with the coating material is adjacent the dispensing head, thereby preventing the coating material from being dispensed from the dispensing head, wherein the step of controlling the dispensing of coating material such that the coating material is not dispensed from the dispensing head comprises refraining from dispensing the coating material onto junctions between struts of the stent.

15. The method of claim 14 wherein the coating material comprises a therapeutic agent.

16. The method of claim 14 wherein the coating material comprises a therapeutic agent suspended in a polymer.

17. The method of claim 14 wherein the step of controlling the dispensing of coating material such that the coating material is not dispensed from the dispensing head further comprises refraining from dispensing the coating material into spaces between struts of the stent.

18. The method of claim 14 wherein the step of moving at least one of the stent or the dispensing head includes rotating the stent.

19. The method of claim 14 wherein the step of moving at least one of the stent or the dispensing head includes sliding the dispensing head in a linear direction.

* * * * *

UNITED STATES PATENT AND TRADEMARK OFFICE
CERTIFICATE OF CORRECTION

PATENT NO. : 7,037,552 B2  Page 1 of 1
APPLICATION NO. : 10/737256
DATED : May 2, 2006
INVENTOR(S) : Zhong et al.

It is certified that error appears in the above-identified patent and that said Letters Patent is hereby corrected as shown below:

Column 4:
    Line 45, "anti-inflanimatory" should read --anti-inflammatory--;
    Line 48, "mesalanline" should read --mesalamine--; and
    Line 59, "chioromethyl" should read --chloromethyl--.

Column 12:
    Line 26, "iunctions" should read --junctions--.

Signed and Sealed this

Twenty-eighth Day of November, 2006

JON W. DUDAS
*Director of the United States Patent and Trademark Office*